United States Patent [19]

Ondetti et al.

[11] 4,234,489
[45] Nov. 18, 1980

[54] PYROGLUTAMIC ACID DERIVATIVES AND ANALOGS

[75] Inventors: Miguel A. Ondetti, Princeton; Eric M. Gordon, Pennington; Denis E. Ryono, Princeton, all of N.J.

[73] Assignee: E. R. Squibb & Sons, Inc., Princeton, N.J.

[21] Appl. No.: 51,772

[22] Filed: Jun. 25, 1979

[51] Int. Cl.³ .................... C07D 207/36; A61K 31/40
[52] U.S. Cl. .......................... 260/326.42; 260/326.2; 260/326.25; 260/326.47; 424/274
[58] Field of Search ...................... 260/326.25, 326.42, 260/326.2, 326.47

[56] References Cited

U.S. PATENT DOCUMENTS

| | | | |
|---|---|---|---|
| 4,091,024 | 5/1978 | Ondetti | 260/326.25 |
| 4,105,776 | 8/1978 | Ondetti et al. | 424/274 |

OTHER PUBLICATIONS

D. B. Miller et al., J. Chem. Soc. (C) (1968) pp. 242–245.

Primary Examiner—Donald G. Daus
Assistant Examiner—M. C. Eakin
Attorney, Agent, or Firm—Lawrence S. Levinson; Donald J. Barrack

[57] ABSTRACT

Pyroglutamic acid derivatives and analogs having the formula

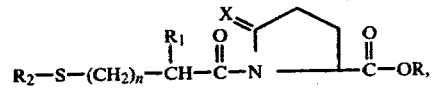

and salts thereof, wherein
R is hydrogen, alkyl or diphenylmethyl;
$R_1$ is hydrogen, alkyl or trifluoromethyl;
$R_2$ is hydrogen,

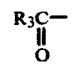

or

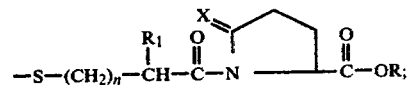

$R_3$ is hydrogen, alkyl, phenyl, or phenylalkyl;
X is oxygen or sulfur; and
n is 0 or 1;
have useful hypotensive activity.

17 Claims, No Drawings

PYROGLUTAMIC ACID DERIVATIVES AND ANALOGS

RELATED APPLICATIONS

U.S. patent application Ser. No. 972,314, filed Dec. 22, 1978 by John Krapcho discloses ketal and thioketal derivatives (acyclic and cyclic) of mercaptoacyl prolines, which are described as useful as antihypertensive agents. The application describes a procedure for preparing the anti-hypertensive products which utilizes an intermediate of the formula

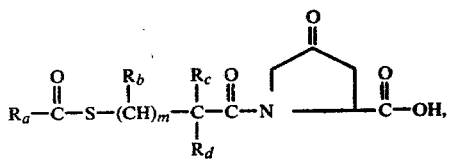

wherein $R_a$ is lower alkyl, phenyl-lower alkyl, phenyl or substituted phenyl; $R_b$, $R_c$, and $R_d$ each is hydrogen or lower alkyl; and m is 0, 1 or 2.

BACKGROUND OF THE INVENTION

The recent prior art contains many disclosures describing mercaptoacyl derivatives of amino acids. Exemplary of these disclosures is U.S. Pat. No. 4,105,776, issued Aug. 8, 1978, which discloses compounds having the formula

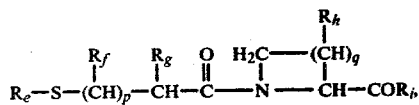

wherein, inter alia, $R_e$ is hydrogen, acyl or

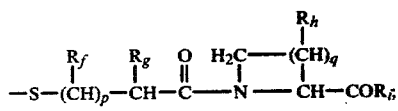

$R_f$ and $R_g$ each is hydrogen, lower alkyl, phenyl or phenyl-lower alkyl; $R_h$ is hydrogen, hydroxy or lower alkyl; $R_i$ is hydroxy, $NH_2$ on lower alkoxy; p is 0, 1 or 2; and q is 1, 2 or 3. The compounds are described as angiotensin converting enzyme inhibitors, useful in the treatment of hypertension.

BRIEF DESCRIPTION OF THE INVENTION

Compounds having the formula

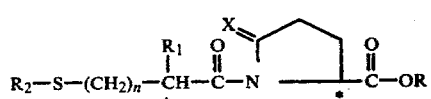

and salts thereof, have useful antihypertensive activity. In formula I, and throughout the specification, the symbols are as defined below.

R is hydrogen, alkyl or diphenylmethyl;
$R_1$ is hydrogen, alkyl or trifluoromethyl;
$R_2$ is hydrogen,

or

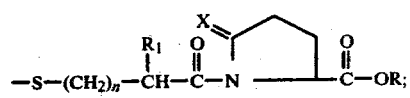

$R_3$ is hydrogen, alkyl, phenyl, or phenylalkyl;
X is oxygen or sulfur; and
n is 0 or 1.

The term "alkyl", as used throughout the specification, either by itself or as part of a larger group, refers to groups having 1 to 7 carbon atoms.

DETAILED DESCRIPTION OF THE INVENTION

The pyroglutamic acid derivatives of formula I, wherein $R_2$ is

can be prepared by reacting a compound having the formula

wherein M is a cation, preferably an alkali metal, with a thio acid having the formula

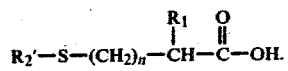

In formula III, and throughout the specification, the symbol $R_2'$ is

The reaction can be accomplished using any one of the numerous techniques well known in the art. Preferably, the thio acid of formula III will first be activated, e.g. by formation of its mixed anhydride, symmetrical anhydride acid chloride or active ester, or by the use of Woodward reagent K or N-ethoxycarbonyl-2-ethoxy-1,2-dihydroquinoline. The preferred method of activation is the formation of the acid chloride.

An alternate (and preferred) procedure for the preparation of the products of formula I (wherein $R_2$ is

comprises first silylating pyroglutamic acid or its thio analogue, 5-thioxoproline. The silylation can be accomplished using well known silyl transfer reagents, e.g., bis-trimethylsilylacetamide or bis-trimethylsilyltrifluoroacetamide. The silylated intermediate, e.g.,

need not be isolated from its reaction mixture prior to reaction with an activated derivative of a thio acid of formula III to yield the corresponding product of formula I wherein $R_2$ is

The compounds of formula I wherein $R_2$ is hydrogen can be prepared from a corresponding compound of formula I wherein $R_2$ is

by treatment with alkali or ammonia under carefully controlled conditions, or by treatment with mercuric trifluoroacetate followed by hydrogen sulfide.

The "bis compounds" of formula I, i.e. those compounds wherein $R_2$ is

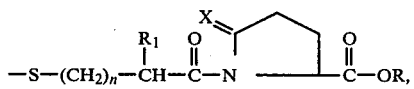

can be obtained by oxidation of the corresponding compound of formula I (wherein $R_2$ is hydrogen) with iodine.

The products of formula I have at least one asymmetric carbon atom. If $R_1$ is other than hydrogen, the products have two asymmetric carbon atoms (these are indicated by asterisks in formula I). The compounds, therefore, exist in stereoisomeric forms or in racemic mixtures thereof. All of these are within the scope of this invention. The synthesis described above can be run using reactants that are racemic mixtures or stereoisomers. When the reactants are racemic mixtures, the stereoisomers of the resulting product can be separated using art recognized techniques. The L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product.

The compounds of formula I, and the alkyl esters and salts thereof, are useful as antihypertensive agents. They inhibit the conversion of the decapeptide angiotensin I to angiotensin II and, therefore, are useful in reducing or relieving angiotensin related hypertension. The action of the enzyme resin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 50 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated as obtained.

The following examples are specific embodiments of this invention.

EXAMPLE 1

1-[3-(Acetylthio)-2-methyl-1-oxopropyl]-5-oxo-L-proline, dicyclohexylamine salt, isomers A and B L-Pyroglutamic acid (4.5 g, 35 mmol.) is suspended in a mixture of 35 ml of propylene oxide and 210 ml of dry acetonitrile at room temperature. Bis-trimethylsilyl-trifluoroacetamide (20.4 ml, 77 mmol) is added and the stoppered reaction is stirred at room temperature for 15 minutes. 3-(Acetylthio)-2-methylpropionyl chloride (5.7 ml, 36.8 mmol) is added and the reaction stirred for about 11 hours. The reaction is then chilled in an ice-bath and slowly treated with 35 ml of 1 N hydrochloric acid and stirred for five minutes. Acetonitrile is then removed in vacuo and the resulting oil dissolved in 400 ml of ethylacetate. The organic solution is rinsed with three 70 ml portions of water and brine, dried over sodium sulfate and concentrated in vacuo to 16.8 g of oil. The crude mixture is dissolved in 900 ml of ethyl ether and treated with 7 ml (35.1 mmol) of dicyclohexylamine. The first crop (7.1 g, melting point 194°–196° C.) is recrystallized from methanol/ethyl ether to yield 5.1 g of isomer A, dicyclohexylamine salt plus a further 0.65 g from the mother liquor. Total yield of isomer A is 5.75 g, melting point 197°–199° C.; $[\alpha]_D = -70.5°$ (c=1, MeOH).

The first mother liquor is concentrated and cooled to yield a first crop of isomer B (5.4 g, melting point 162°–164° C.) which upon recrystallization from methanol/ethyl ether gives isomer B, dicyclohexylamine salt, 3.5 g, melting point 168°–169° C.; $[\alpha]_D = +6.2°$ (c=1, MeOH).

EXAMPLE 2

1-[3-(Acetylthio)-2-methyl-1-oxopropyl]-5-oxo-L-proline, lithium salt, isomer A 1-[3-(Acetylthio)-2-methyl-1-oxopropyl]-5-oxo-L-proline, dicyclohexylamine salt, isomer A, is converted to the corresponding lithium salt by passing it through a 20 equivalent AG50W-X2 cation exchange resin (Li⊕) (composed of sulfonic acid exchange groups, lithium form, attached to a styrene-divinylbenzene polymer lattice) column. The column is packed in water and the dicyclohexylamine salt is dissolved in a mixture of 100 ml of water and 50 ml of methanol, applied to the column and eluted with water. The procedure is repeated a second time for complete conversion to the lithium salt and the lyophilized product is recrystallized from methanol/ethyl ether to afford 1.13 g of the title compound, melting point 216°–217° C., dec.

EXAMPLE 3

1-[3-(Acetylthio)-2-methyl-1-oxopropyl]-5-oxo-L-proline, lithium salt, isomer B 1-[3-(Acetylthio)-2-methyl-1-oxopropyl]-5-oxo-L-proline, dicyclohexylamine salt, isomer B (3.0 g., 6.6 mmol) is dissolved in approximately 35 ml. of a 2:1 methanol:water mixture and exchanged on a 40 equivalent AG50W-X2 cation exchange resin (H⊕) (composed of sulfonic acid exchange groups, free acid form, attached to a styrene-divinyl polymer lattice) column eluted with water. The resulting product fractions show impurities on silica gel thin layer chromatography; $R_f$ of isomer B free acid=0.65; $R_f$ of impurities=0.9 and 0.4; solvent is 60:20:6:11, ethyl acetate:pyridine:acetic acid; water. Lyophilization of the pooled fractions gives 1.5 g of impure product. Complete separation of the desired product from impurities is achieved by chromotography on 120 g of E. Merck Silica Gel 60 packed and eluted with 130:20:6:11, ethyl acetate:pyridine:acetic acid:water (flow rate is approximately 100 ml/minute). The product fractions give 1.8 g of an oil which is then passed once through about 500 ml of LH-20, (bead formed dextran gel), lyophilized and finally exchanged on a 40 equivalent AG50W-X2 cation exchange (Li⊕) column eluting with water. Lyophilization affords 1.3 g of the title compound as a monohydrate, melting point 204°–205° C.

EXAMPLE 4

1-(3-Mercapto-2-methyl-1-oxopropyl)-5-oxo-L-proline, isomer A

1-[3-(Acetylthio)-2-methyl-1-oxopropyl]-5-oxo-L-proline, dicyclohexylamine salt, isomer A (7 g, 15.4 mmol) is converted to the free acid by partitioning between 170 ml of 0.2 N aqueous sulfuric acid and five 40 ml portions of ethyl acetate. Work-up yields crude free acid, which is dissolved in 150 ml of dry acetonitrile and 1.14 ml of dry methanol at room temperature. The resulting solution is then treated with 6.61 g (15.2 mmol) of mercuric trifluoroacetate and stirred at room temperature for 3.5 hours. The heterogeneous reaction mixture is cooled in an ice-bath and treated with hydrogen sulfide for three minutes, purged with nitrogen for ten minutes, filtered over Celite and concentrated in vacuo to 3.4 g of a crude semi-solid. Trituration with warm ethyl acetate/hexane yields 2.67 g of material, melting point 101°–108° C. This material is dissolved in 200 ml of ethyl acetate and rinsed with 15 ml of 10% potassium sulfate, water and brine, dried over sodium sulfate and concentrated in vacuo to a crystalline solid which is triturated with hexanes to afford 2.49 g of the title compound, melting point 104°–106.5° C.

EXAMPLE 5

[1(S)]-1-[3-(Acetylthio)-2-methyl-1-oxopropyl]-5-thioxo-L-proline, diphenylmethyl ester (a) 5-Thioxo-L-proline, diphenylmethyl ester A mixture of 26.0 g (88 mmol) of L-pyroglutamic acid, diphenylmethyl ester and 19.5 g (88 mmol) of phosphorous pentasulfide in 400 ml of pyridine is refluxed under nitrogen for 1½ hours. After cooling to room temperature, the reaction mixture is poured into 400 ml of water and extracted with three 1 liter portions of ethyl acetate. The organic extract is washed with four 1 liter portions of water, 1 liter of saturated aqueous sodium bicarbonate, dried (Na₂SO₄) and concentrated. Chromatography of the residue on 400 g of silica gel, eluting with methylene chloride gives 14.6 g of crude product. Recrystallization from ethyl-acetate/hexanes affords 10.5 g of the title compound melting point 177°–178° C.

(b) [1(S)]-1-[3-(Acetylthio)-2-methyl-1-oxopropyl]-5-thioxo-L-proline, diphenylmethyl ester To a solution of 500 mg (1.6 mmol) of 5-thioxo-L-proline, diphenylmethyl ester in 10 ml of methylene chloride cooled in an ice-bath under nitrogen is added 0.218 ml (1.56 mmol) of triethylamine followed by a solution of 0.25 ml (1.62 mmol) of (S)-3-(acetylthio)-2-methylpropionyl chloride dissolved in 12 ml of methylene chloride which is added over a 10 minute period. The reaction mixture is stoppered and stirred at 5° C. for a period of about 15 hours. The solution is then taken up in 100 ml of ethyl acetate and rinsed with two 20 ml portions of 10% potassium sulfate, 20 ml of water, 30 ml of saturated aqueous sodium bicarbonate, brine and dried (Na₂SO₄). Removal of solvent in vacuo gives an oil which is chromatographed on 75 g of silica gel eluted with 50:1, dichloromethane:ethyl acetate. The product is obtained as an oil, 724 mg with $R_f$=0.5 (dichloromethane, silica gel).

EXAMPLE 6

[1(S)]-1-[3-(Acetylthio)-2-methyl-1-oxopropyl]-5-thioxo-L-proline, dicyclohexylamine salt A solution of 265 mg (0.582 mmol) of [1(S)]-1-[3-(acetylthio)-2-methyl-1-oxopropyl]-5-thioxo-L-proline, diphenylmethyl ester and 0.7 ml of anisole in 5 ml of methylene chloride is cooled in an ice-bath under nitrogen and treated with 2.2 ml of trifluoroacetic acid. The reaction mixture is kept at ice-bath temperatures for 1½ hours, concentrated in vacuo and the crude product dried for about 16 hours in vacuo in the presence of potassium hydroxide. The residue is dissolved in a minimal amount of ethyl acetate and treated with a slight excess of dicyclohexylamine. The product dicyclohexylamine salt is precipitated by the addition of ether.

EXAMPLE 7

[1(S)]-1-(3-Mercapto-2-methyl-1-oxopropyl)-5-thioxo-L-proline

By substituting [1(S)]-1-[3-(acetylthio)-2-methyl-1-oxopropyl]-5-thioxo-L-proline, dicyclohexylamine salt for 1-[3-(acetylthio)-2-methyl-1-oxopropyl]-5-oxo-L-proline, dicyclohexylamine salt, isomer A in the procedure of Example 4, [1(S)]-1-(3-mercapto-2-methyl-1-oxopropyl)-5-thioxo-L-proline is obtained.

EXAMPLE 8

1-[3-(Acetylthio)-2-methyl-1-oxopropyl]-5-thioxo-L-proline, dicyclohexylamine salt, isomers A and B (a) 5-Thioxo-L-proline A solution of 5.9 g (18.9 mmol) of 5-thioxo-L-proline, diphenylmethyl ester in 25 ml of dioxane is added dropwise over a period of 15 minutes to 28.5 ml of 1 N aqueous sodium hydroxide which is cooled in an ice-bath. The reaction mixture is stoppered and stirred at ice-bath temperatures for 1½ hours, then at ambient temperature for 30 minutes. At the end of this time 50 ml of water is added to the reaction and the solution is rinsed with two 50 ml portions of ether. The aqueous layer is cooled and acidified to pH 1 with concentrated hydrochloric acid and extracted with five 100 ml portions of ethyl acetate. The organic extract is rinsed with brine, dried ($Na_2SO_4$) and concentrated in vacuo. The residue obtained is dissolved in 30 ml of ethyl acetate and treated with 4.1 ml (20.8 mmol) of dicyclohexylamine. Addition of ether affords 4.7 g of a solid product, melting point 215°–216° C. (d). The salt is then converted to the free acid by partitioning between 0.2 N sulfuric acid and ethyl acetate. Drying ($Na_2SO_4$) of the ethyl acetate extract yields 5-thioxo-L-proline.

(b) 1-[3-(Acetylthio)-2-methyl-1-oxopropyl]-5-thioxo-L-proline, dicyclohexylamine salt, isomers A and B By substituting 5-thioxo-L-proline for L-pyroglutamic acid in the procedure of Example 1, 1-[3-(acetylthio)-2-methyl-1-oxopropyl]-5-thioxo-L-proline, dicyclohexylamine salt, isomers A and B are obtained.

What is claimed is:

1. A compound having the formula

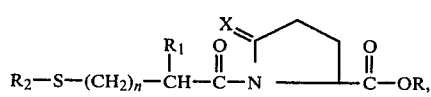

or a salt thereof, wherein
R is hydrogen, alkyl or diphenylmethyl;
$R_1$ is hydrogen, alkyl or trifluoromethyl;
$R_2$ is hydrogen,

or

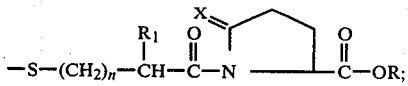

$R_3$ is hydrogen, alkyl, phenyl, or phenylalkyl;
X is oxygen or sulfur; and
n is 0 or 1 wherein "alkyl" refers to groups of 1 to 7 carbon atoms.

2. A compound in accordance with claim 1 wherein R is hydrogen.

3. A compound in accordance with claim 1 wherein R is alkyl.

4. A compound in accordance with claim 1 wherein R is diphenylmethyl.

5. A compound in accordance with claim 1 wherein $R_2$ is hydrogen.

6. A compound in accordance with claim 1 wherein $R_2$ is

7. A compound in accordance with claim 1 wherein $R_2$ is

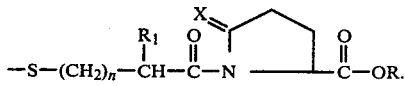

8. A compound in accordance with claim 1 wherein X is oxygen.

9. A compound in accordance with claim 1 wherein X is sulfur.

10. A compound in accordance with claim 1 wherein n is 0.

11. A compound in accordance with claim 1 wherein n is 1.

12. The compound in accordance with claim 1, 1-[3-(acetylthio)-2-methyl-1-oxopropyl]-5-oxo-L-proline, dicyclohexylamine salt.

13. The compound in accordance with claim 1, [3-(acetylthio)-2-methyl-1-oxopropyl]-5-oxo-L-proline, lithium salt.

14. The compound in accordance with claim 1, 1-(3-mercapto-2-methyl-1-oxopropyl)-5-oxo-L-proline.

15. The compound in accordance with claim 1, [1(S)]-1-[3-(acetylthio)-2-methyl-1-oxopropyl]-5-thioxo-L-proline, diphenylmethyl ester.

16. The compound in accordance with claim 1, 1-[3-(acetylthio)-2-methyl-1-oxopropyl]-5-thioxo-L-proline, dicyclohexylamine salt.

17. The compound in accordance with claim 1, [1(S)]-3-mercapto-2-methyl-1-oxopropyl]-5-thioxo-L-proline.

* * * * *